United States Patent [19]

Boussouira et al.

[11] Patent Number: 6,153,205

[45] Date of Patent: Nov. 28, 2000

[54] TOPICAL APPLICATION PRODUCT CONTAINING A LIPASE, A VITAMIN PRECURSOR AND A FATTY ALCOHOL

[75] Inventors: Boudiaf Boussouira, Paris; Dang-Man Pham, Sucy En Brie, both of France

[73] Assignee: L'Oreal, Paris, France

[21] Appl. No.: 09/348,672

[22] Filed: Jul. 6, 1999

[30] Foreign Application Priority Data

Jul. 6, 1998 [FR] France ................................. 98 08615

[51] Int. Cl.⁷ ...................................................... A61K 7/00
[52] U.S. Cl. ........................... 424/401; 424/59; 514/844; 514/846; 514/847; 514/937
[58] Field of Search ....................... 424/401, 59

[56] References Cited

U.S. PATENT DOCUMENTS 5,788,972  8/1998  De Salvert et al. .................... 424/401

FOREIGN PATENT DOCUMENTS

| 0 487 404 | 5/1992 | European Pat. Off. . |
| 0 710 478 | 5/1996 | European Pat. Off. . |
| 2 101 044 | 3/1972 | France . |
| 03109311 | 9/1991 | Japan . |

*Primary Examiner*—Shelley A. Dodson
*Assistant Examiner*—Konata M. George
*Attorney, Agent, or Firm*—Oblon, Spivak, McClelland, Maier & Neustadt, P.C.

[57] ABSTRACT

A product suitable for topical application to skin, containing at least one enzyme which is a lipase, at least one precursor of a vitamin used in cosmetics and/or dermatology, which is an ester comprising at least one ester function with a linear or branched, saturated or unsaturated chain containing from 2 to 25 carbon atoms, and at least one $C_6$ to $C_{22}$ alcohol, where the weight ratio between the alcohol and the precursor is from 0.25 to 30/1, with the exception of alcohol/precursor combinations consisting of (1) cetyl alcohol/ascorbyl palmitate with a weight ratio of 4/1, and (2) stearyl alcohol/retinyl palmitate with a weight ratio of 1/0.6. According to a preferred form of the invention, the precursor and the lipase are packaged so as not to be in contact with each other until they are applied to the skin.

27 Claims, No Drawings

TOPICAL APPLICATION PRODUCT CONTAINING A LIPASE, A VITAMIN PRECURSOR AND A FATTY ALCOHOL

BACKGROUND OF THE INVENTION

1. Field of the Invention

The present invention relates to a poduct for topical application which can release a cosmetic and/or dermatological active agent on the skin, and to the use of the product for the cosmetic and/or dermatological treatment of the skin, including the scalp.

2. Discussion of the Background

It is well-known to introduce active agents into cosmetic and/or dermatological compositions in order to allow specific skin treatments, for example to combat the drying-out, ageing or pigmentation of the skin, to treat acne or certain skin diseases (eczema, psoriasis), to combat excess weight or to promote the restructuring of the skin or its cell renewal.

For example, ascorbic acid (or vitamin C) is known to stimulate the growth of connective tissue, and in particular that of collagen. It thus strengthens the skin tissue's defences against external attack such as ultraviolet radiation or pollution. It is also used to remove skin pigmentation and marks, as well as to promote cicatrization of the skin.

It is also known that the application of retinol, or vitamin A, in particular combats ageing of the skin and certain skin conditions such as acne or keratinization or cicatrization disorders.

In addition, tocopherols, such as vitamin E, are known to have antioxidant properties with respect to the phospholipids of the cell membrane and radical-scavenging properties (see "Radicaux libres et Vitamine E [Free Radicals and Vitamin E]" by J. B. Chazan and M. Szulc-Cah. Nutr. Diet. 1987, 6, 1, XXII, pages 66 to 76).

Unfortunately, certain active agents, and in particular those mentioned above, are unstable and are sensitive to external factors such as light and heat. This instability goes against the desired efficacy and, what is more, can be the source of unpleasant sensations for the user, for example when the instability of the active agent leads to changes in the color and/or odor of the composition containing it.

Thus, various means have been envisaged to stabilize these active agents. One of these means consists, for example, in blocking the reactive site of the active agent by esterification with, in particular, phosphate, sulphate or alkyl derivatives and in using these derivatives in place of the free active agent. Unfortunately, these derivatives are less effective than the free active agent.

It has also been envisaged to use precursors of such active agents, which, after applying them to the skin, are cleaved by the skin enzymes and thus release the free active agent. Thus, EP-A-487,404 discloses the use of a glucosyl derivative of ascorbic acid in dermatological compositions, which is readily hydrolysed by the skin enzymes and thus capable of releasing ascorbic acid when these compositions are applied to the skin. However, the use of such derivatives does not allow a rapid release of ascorbic acid in sufficient quantity on the surface of the skin.

There is thus a need for a topical application product containing vitamins used in cosmetics and/or dermatology, in which these vitamins conserve all their properties and thus their efficacy over time.

EP 710,478 describes that the use of a specific enzyme, lipase, combined with esters of unstable vitamins, such as vitamin A (retinol) or vitamin C (ascorbic acid), avoids the drawbacks of previously known compositions.

SUMMARY OF THE INVENTION

The present inventors have discovered that the rapid release of vitamins in sufficient amount can be enhanced by introducing $C_6$ to $C_{22}$ alcohols into composition containing lipase and esters of unstable vitamins.

Accordingly, the present invention relates to a product for topical application, which comprises at least one enzyme which is a lipase, at least one precursor of a vitamin used in cosmetics and/or dermatology which is an ester comprising at least one ester function with a linear or branched, saturated or unsaturated chain containing from 2 to 25 carbon atoms, and at least one $C_6$ to $C_{22}$ alcohol, where the weight ratio between the alcohol and the precursor is from 0.25 to 30/1, with the exception of alcohol/precursor combinations consisting of (1) cetyl alcohol/ascorbyl palmitate with a weight ratio of 4/1, and (2) stearyl alcohol/retinyl palmitate with a weight ratio of 1/0.6.

The present invention also relates to methods of treating skin, including the scalp, with the inventive product.

The present invention also relates to methods of preparing the inventive product.

A more complete appreciation of the invention and many of the attendant advantages thereof will be readily obtained as the same becomes better understood by reference to the following detailed description.

DETAILED DESCRIPTION OF THE INVENTION

The weight ratio between the alcohol and the precursor is preferably from 1 to 25/1 and preferably from 2 to 20/1, and even more preferably from 5 to 15/1. These ranges include all specific values and subranges therebetween, such as 3/1, 8/1, 10/1, 12/1, 18/1 and 22/1.

As used herein, the term "product" refers both to the cosmetic or dermatological composition in which two or more components, e.g., lipase and precursor, are in physical admixture and to an article which comprises a container in which the enzyme and the precursor are housed, isolated from each other.

A lipase is an enzyme which is known to hydrolyse triglycerides into mono- and diglycerides, into glycerol and into free fatty acids. It is used in particular in detergents see the article "Lipases as detergent components", H. Andree et al., Journal of Applied Biochemistry, 1980, Vol. 2, pages 218 to 229, incorporated herein by reference, in order to allow the removal of greasy stains such as those from frying fats, from oils, from sebum or from greasy cosmetics such as lipsticks. On account of its property of cleaving triglycerides, it has been used in the cosmetics field in immobilized form to cleanse the skin (see, for example, U.S. Pat. No. 4,556,554, incorporated herein by reference).

The lipase used in the present invention must be stable enough to conserve its enzymatic activity. It belongs to the group of enzymes of classification EC 3.1.1.3., which corresponds to a lipase which cleaves the ester bonds in positions 1 and 3 of a triglyceride. The lipase may be "lipase SP644" and "lipolase 100 L" available from Novo Nordisk.

The lipase can be used in the inventive composition in an amount ranging from 0.05% to 30% by weight, preferably from 0.1 to 10% by weight, relative to the total weight of the composition, and more preferably from 0.1 to 5% by weight relative to the total weight of the composition. These ranges include all specific values and subranges therebetween, such as 0.075, 0.2, 0.5, 1, 2, 3, 8, 12, 15, 20 and 25% by weight.

As used herein, the term "precursor of a vitamin" refers to a esterified vitamin which is hydrolyzed on the skin to produce the free vitamin. Vitamins suitable in the present invention include those which comprising at least one hydroxyl function, and in particular esterifiable vitamins such as retinol (vitamin A) and derivatives thereof, tocopherol or its derivatives, and ascorbic acid (vitamin C) and derivatives thereof.

The ester of the inventive composition comprises one or more ester functions with a linear or branched, saturated or unsaturated chain containing from 2 to 25 carbon atoms, optionally comprising one or more substituents. The ester functions may be of the formula—O—C(=O)—R in which R has 1 to 24 carbons. The chain of the ester function is chosen in particular from acyl, benzoyl, alkylbenzoyl, acylbenzoyl and 2-hydroxyphenylacetyl radicals, which are optionally substituted. The substituent may be, in a preferred embodiment, a hydroxylated radical. According to one preferred embodiment of the invention, the chain of the ester function contains from 12 to 18 carbon atoms.

The precursor is, for example, an ester of a vitamin esterified with an acid chosen from lauric acid, palmitic acid, stearic acid, cetylic acid, myristic acid, linoleic acid, octanoic acid or oleic acid esters, or alternatively from butyric acid, propionic acid or acetic acid esters or else from esters of a hydroxy acid such as salicylic acid or lactic acid, or mixtures of these esters.

The ester may be, for example, dihydroxyacetone mono- and dilaurate, dihydroxyacetone mono- and distearate, dihydroxyacetone mono- and dipalmitate, ascorbyl palmitate, ascorbyl laurate, ascorbyl myristate, ascorbyl stearate, ascorbyl nicotinate, tocopheryl acetate, tocopheryl linoleate, retinyl palmitate, retinyl propionate, retinyl acetate, retinyl butyrate, retinyl octanoate, retinyl laurate, retinyl oleate or retinyl linoleate.

The ester may be present in the inventive composition in an amount ranging from 0.1 to 50% by weight and preferably from 0.5 to 10% by weight relative to the total weight of the composition when it is a vitamin ester, and from 5 to 30% by weight relative to the total weight of the composition when it is a ketone ester and in particular a dihydroxyacetone ester. These ranges include all specific values and subranges therebetween, such as 0.2, 0.75, 1, 2, 8, 10, 12, 15, 20 and 25% by weight.

The $C_6$ to $C_{22}$ alcohols used according to the invention are preferably alcohols whose carbon chain is saturated or unsaturated, and linear, branched or cyclic. Examples of the alcohol include cetyl alcohol, stearyl alcohol, isostearyl alcohol, cetylstearyl alcohol, behenylstearyloctyldodecanol, menthol and cholesterol. Mixtures of different alcohols may be used.

In one embodiment the $C_6$ to $C_{22}$, preferably $C_8$ to $C_{22}$, alcohols used are those whose carbon chain is saturated or unsaturated, and linear or branched. Specific examples include cetyl alcohol, stearyl alcohol, isostearyl alcohol, cetylstearyl alcohol, and behenylstearyloctyldodecanol.

In one embodiment, the composition lacks $C_6$ to $C_{22}$ acids and esters of $C_6$ to $C_{22}$ acids, such as stearic acid, and glyceryl $C_6$ to $C_{22}$ mono-, di- or triesters.

In one embodiment, the lipase, the precursor, and the $C_6$ to $C_{22}$ alcohols are combined to form a single composition, which is preferably prepared just before use.

In another embodiment, the lipase and the precursor are packaged so as not to be in contact with each other, for example in two separate compositions which either can be mixed together at the time of application or can be applied successively or separately in time.

According to this second variant, the $C_6$ to $C_{22}$ alcohols used according to the invention can be included in one or other of the compositions, optionally in both compositions.

The compositions may be placed, for example, in two compartments, which are in communication with a common channel, as a result of which they can leave while being mixed together before application to the skin. Such two-compartment packaging devices are described, for example, in FR-A-2,045,559, FR-A-2,105,332, FR-A-2,258,319, FR-A-2,293,375, FR-A-2,586,913 or FR-A-2,643,615, each incorporated herein by reference.

One of the compositions can also be prepared in encapsulated form and/or in the form of microcapsules or microgranules immersed in the other composition, the microcapsules or microgranules being crushed at the time of application by rubbing on the skin, thus allowing mixing of the lipase, the precursor and the $C_6$ to $C_{22}$ alcohols and release of the free vitamin on the skin.

As discussed above, products are excluded in which the alcohol/precursor is of (1) cetyl alcohol/ascorbyl palmitate at a weight ratio of 4/1, and (2) stearyl alcohol/retinyl palmitate at a weight ratio of 1/0.6. In one embodiment, products containing cetyl alcohol/ascorbyl palmitate or stearyl alcohol/retinyl palmitate are excluded. In another embodiment, products containing at least one of cetyl alcohol, ascorbyl palmitate, stearyl alcohol and retinyl palmitate are excluded.

The product of the invention may be used, depending on the vitamin ester it contains, for the cosmetic and/or dermatological treatment of the skin. When used for this purpose the product preferably comprises a medium which is suitable for topical application o skin. In one embodiment, the product is in the form dermatological salve or ointment suitable for topical application to skin.

The product as described above may also be used for the cosmetic treatment of the skin. When used to treat skin, the product may be topically applied to the skin surface. The product may be applied with the fingers, for example.

Another aspect of the present invention is a cosmetic process for treating the skin, in which an enzyme, which is a lipase, and at least one precursor of a vitamin used in cosmetics or dermatology, which is an ester comprising at least one ester function with a linear or branched, saturated or unsaturated chain containing from 2 to 25 carbon atoms, as described above, is applied to the skin in the presence of at least one $C_6$ to $C_{22}$ alcohol, simultaneously or separately in time, where the weight ratio between the alcohol and the precursor is from 2 to 30/1, with the exception of the combination consisting of cetyl alcohol/ascorbyl palmitate with a weight ratio of 4/1. From this process applying cetyl alcohol/ascorbyl palmitate or stearyl alcohol/retinyl palmitate may also be excluded. Also excluded may be applying at least one of cetyl alcohol, ascorbyl palmitate, stearyl alcohol and retinyl palmitate.

The cosmetically and/or dermatologically acceptable medium generally comprises water or a mixture of water and fatty substances, or a mixture of fatty substances.

As fatty substances which can be used in the invention, examples include mineral oils (petroleum jelly, mineral oil), plant oils and their hydrogenated derivatives, animal oils, synthetic oils, silicone oils (dimethicone, cyclomethicone) and fluoro oils. Fatty acids and waxes can also be mentioned as other fatty substances.

In particular, the product can be in the form of aqueous, alcoholic or aqueous-alcoholic solutions, hydrophilic or lipophilic gels, microemulsions, water-in-oil or oil-in-water or water-in-oil-in-water or oil-in-water-in-oil emulsions having the appearance of a cream or a gel, which are optionally capable of forming a foam, in the form of an aerosol, or in the form of vesicle dispersions containing ionic and/or nonionic lipids. These pharmaceutical forms are prepared according to the usual methods of the fields concerned.

The medium which is suitable for topical application according to the invention can also contain well-known adjuvants that are common in the cosmetics or dermatological field, such as hydrophilic or lipophilic gelling agents, surfactants, hydrophilic or lipophilic active agents, preserving agents, antioxidants, solvents, fragrances, fillers, screening agents and dyestuffs. The amounts of the various constituents of the product according to the invention are those used conventionally in the fields concerned.

Of course, one skilled in the art will not introduce into this product compounds which are of a nature and in an amount which interfere the use of the product for topical application to skin.

The inventive product may, in preferred embodiments, constitute protective, treatment or care products for the face, for the neck, for the hands or for the body, artificial tanning products or products for the hair, and in particular for conditioning the scalp, for example in the form of shampoos, conditioning lotions, styling creams or gels and lotions or gels for preventing hair loss.

EXAMPLES

Having generally described this invention, a further understanding can be obtained by reference to certain specific examples which are provided herein for purposes of illustration only and are not intended to be limiting unless otherwise specified. The amounts indicated are percentages by weight, except where mentioned otherwise.

EXAMPLE 1

Influence of alcohols on the hydrolysis of 0.1% retinyl palmitate in the presence of 0.1% lipase.

Various alcohols are tested at 1% with 0.1% retinyl palmitate in the presence of 0.1% lipase in a medium: 40/60% heptane/$H_2O$, 50 mM $CaCl_2$, 16 hours in contact.

The results relating to the percentages of hydrolysis of retinyl palmitate are collated in Table 1 below.

TABLE 1

| Test compound | % of hydrolysis |
|---|---|
| Control | 23 |
| Stearyl alcohol | 94 |
| Isostearyl alcohol | 95 |
| Cetyl alcohol | 94 |
| Cetylstearyl alcohol | 94 |
| Menthol | 48 |
| Cholesterol | 30 |
| Behenylstearyloctyldodecanol | 93 |

It is thus observed that the degree of hydrolysis of retinyl palmitate is greatly increased in the presence of the alcohols as defined in the present invention.

EXAMPLE 2

Influence of different contents of isostearyl alcohol on the hydrolysis of 0.1% retinyl palmitate in the presence of 0.1% lipase.

Different isostearyl alcohol contents are tested with 0.1% retinyl palmitate in the presence of 0.1% lipase in a medium: 40/60% heptane/$H_2O$, 50 mM $CaCl_2$, after reaction for 90 minutes.

The results relating to the percentages of hydrolysis of the retinyl palmitate are collated in Table 2 below.

TABLE 2

| % of isostearyl alcohol | % of hydrolysis |
|---|---|
| 0 | 25% |
| 0.1% | 68% |
| 0.25% | 80% |
| 0.5% | 88% |
| 1% | 90% |
| 2% | 93% |
| 3% | 69% |
| 4% | 56% |
| 6% | 30% |

It is seen in this table that this degree of hydrolysis is very high under the conditions of the present invention, i.e. when the weight ratio between the said alcohol and the said precursor is from 0.25 to 30/1.

EXAMPLE 3

Influence of different stearyl alcohol contents on the hydrolysis of 0.1% retinyl palmitate in the presence of 0.1% lipase.

Different stearyl alcohol contents are tested with 0.1% retinyl palmitate in the presence of 0.1% lipase in a medium: 40/60% heptane/$H_2O$, 50 mM $CaCl_2$, after reaction for 20 hours.

The results relating to the percentages of hydrolysis of the retinyl palmitate are collated in Table 3 below:

TABLE 3

| % of stearyl alcohol | % of hydrolysis |
|---|---|
| 0% | 24% |
| 0.025% | 41% |
| 0.1% | 73% |
| 0.2% | 84% |
| 0.25% | 86% |
| 0.5% | 91% |
| 1% | 95% |

It is seen in this table that this degree of hydrolysis is very high under the conditions of the present invention, i.e. when the weight ratio between the said alcohol and the said precursor is from 0.25 to 30/1.

EXAMPLE 4

| Care cream for depigmenting the skin | |
|---|---|
| Oily phase: | |
| Triceteareth-4 phosphate/sodium $C_{14}$—$C_{17}$ sec-alkyl sulphonate (Hostacerin CG sold by Hoechst Celanese) (surfactant) | 4% |
| Cetyl alcohol | 1% |
| Petroleum jelly | 2% |
| Mineral oil | 4% |
| Dimethicone | 3% |
| Cyclomethicone | 3% |
| Dimethicone copolyol (surfactant) | 1% |
| Triclosan (preserving agent) | 0.1% |
| Ascorbyl palmitate | 1% |
| Aqueous phase: | |
| Propylene glycol (wetting agent) | 2% |
| PEG-20 (organoleptic agent) | 1% |
| Lipolase 100 L | 1% |

EXAMPLE 4-continued

Care cream for depigmenting the skin

| | |
|---|---|
| Phenoxyethanol (preserving agent) | 0.4% |
| Water | qs 100% |

The lipolase 100 L is introduced into the aqueous phase in encapsulated form, in microcapsules also containing atelocollagen and glycosaminoglycans.

These microcapsules are immersed into the rest of the constituents after preparing the emulsion.

EXAMPLE 5

Anti-wrinkle cream

| Oily phase: | |
|---|---|
| Triceteareth-4 phosphate/sodium $C_{14}$—$C_{17}$ sec-alkyl sulphonate (Hostacerin CG sold by Hoechst Celanese) (surfactant) | 5% |
| Stearyl alcohol | 1.5% |
| Petroleum jelly | 2% |
| Mineral oil | 4% |
| Dimethicone | 3% |
| Cyclomethicone | 3% |
| Dimethicone copolyol (surfactant) | 1% |
| triclosan (preserving agent) | 0.1% |
| Retinyl palmitate | 1% |
| Aqueous phase: | |
| Propylene glycol (wetting agent) | 2% |
| PEG-20 (organoleptic agent) | 1% |
| Lipolase 100 L | 1% |
| Phenoxyethanol (preserving agent) | 0.4% |
| Water | qs 100% |

The retinyl palmitate is introduced into the composition in the form of microspheres also containing atelocollagen and glycosaminoglycans.

These microspheres are immersed into the rest of the constituents after preparing the emulsion.

EXAMPLE 6

Anti-wrinkle cream

| Oily phase: | |
|---|---|
| Triceteareth-4 phosphate/sodium $C_{14}$—$C_{17}$ sec-alkyl sulphonate (Hostacerin CG sold by Hoechst Celanese) (surfactant) | 5% |
| Stearyl alcohol | 2% |
| Petroleum jelly | 2% |
| Mineral oil | 4% |
| Phenyl trimethicone | 4% |
| Cyclomethicone | 4% |
| Dimethicone/dimethiconol (surfactant) | 2% |
| Triclosan (preserving agent) | 0.1% |
| Retinyl palmitate | 0.6% |
| Aqueous phase: | |
| Propylene glycol (wetting agent) | 2% |
| PEG-20 (organoleptic agent) | 1% |
| Lipolase SP 644 | 0.5% |
| Phenoxyethanol (preserving agent) | 0.2% |
| Chlorophenesine | 0.2% |
| Polyacrylamide/$C_{13}$—$C_{14}$ isoparaffin/Laureth-7 (Sepigel 305) sold by SEPPIC) (gelling agent) | 0.6% |
| Water | qs 100% |

The retinyl palmitate is introduced into the composition in the form of microspheres also containing atelocollagen and sodium chondroitin sulphate.

These microspheres are immersed in the rest of the constituents after preparing the emulsion.

EXAMPLE 7

Anti-wrinkle cream

| A. Emulsion containing the vitamin A ester: | |
|---|---|
| Oily phase: | |
| Triceteareth-4 phosphate (Hostaphat KW 340 N sold by Clariant) (surfactant) | 5.3% |
| Stearyl alcohol | 3% |
| Petroleum jelly | 5% |
| Mineral oil | 7% |
| Phenyl trimethicone | 3% |
| Cyclomethicone | 6% |
| Triclosan (preserving agent) | 0.1% |
| Retinyl palmitate | 0.3% |
| Aqueous phase: | |
| Glycerol (wetting agent) | 3% |
| Propylene glycol (wetting agent) | 2% |
| PEG-20 (organoleptic agent) | 1% |
| Phenoxyethanol (preserving agent) | 0.6% |
| Imidazolidinylurea (preserving agent) | 0.3% |
| Acrylates copolymer (matt-effect powder) | 0.2% |
| Polyacrylamide/$C_{13}$—$C_{14}$ isoparaffin/Laureth-7 (Sepigel 305 sold by SEPPIC) (gelling agent) | 0.1% |
| Water | qs 100% |
| B Emulsion containing the lipase: | |
| Oily phase: | |
| Triceteareth-4 phosphate (Hostaphat KW 340 N sold by Clariant) (surfactant) | 5.3% |
| Stearyl alcohol | 3% |
| Petroleum jelly | 5% |
| Mineral oil | 7% |
| Phenyl trimethicone | 3% |
| Cyclomethicone | 6% |
| Triclosan (preserving agent) | 0.1% |
| Aqueous phase: | |
| Glycerol (wetting agent) | 3% |
| Propylene glycol (wetting agent) | 2% |
| PEG-20 (organoleptic agent) | 1% |
| Phenoxyethanol (preserving agent) | 0.6% |
| Imidazolidinylurea (preserving agent) | 0.3% |
| Acrylates copolymer (matt-effect powder) | 0.2% |
| Polyacrylamide/$C_{13}$—$C_{14}$ isoparaffin/Laureth-7 (Sepigel 305 sold by SEPPIC) (gelling agent) | 0.1% |
| Lipolase SP 644 | 0.5% |
| Water | qs 100% |

These emulsions are prepared conventionally. They are placed in two separate compartments and are placed in contact with each other at the time of application to the skin.

The retinyl palmitate is introduced at the end of the preparation of emulsion A.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-08615, filed on Jul. 6, 1998, and incorporated herein by reference.

What is claimed is:

1. A product suitable for topical application, comprising:
    a lipase;
    at least one precursor of a vitamin, wherein the precursor is an ester containing at least one ester functional group having a linear or branched, saturated or unsaturated chain containing from 2 to 25 carbon atoms; and at least one $C_6$ to $C_{22}$ alcohol, wherein the weight ratio of the alcohol to the precursor is 0.25 to 30/1, with the proviso that products comprising (1) cetyl alcohol/ascorbyl palmitate at a weight ratio of 4/1, and (2) stearyl alcohol/retinyl palmitate at a weight ratio of 1/0.6 are excluded.

2. The product of claim 1, wherein the weight ratio of alcohol to the precursor is 1 to 25/1.

3. The product of claim 1, wherein the weight ratio of the alcohol to the precursor is 5 to 15/1.

4. The product of claim 1, wherein the chain of the ester function is selected from the group consisting of acyl, benzoyl, alkylbenzoyl, acylbenzoyl and 2-hydroxyphenylacetyl groups, which are optionally substituted.

5. The product of claim 1, wherein the chain of the ester functional group contains from 12 to 18 carbon atoms.

6. The product of claim 1, wherein the precursor is a hydroxyl-containing vitamin esterified with an acid selected from the group consisting of lauric acid, palmitic acid, stearic acid, cetylic acid, myristic acid, propionic acid, linoleic acid, acetic acid, butyric acid, octanoic acid, oleic acid esters, and mixtures thereof.

7. The product of claim 1, wherein the vitamin comprises at least one hydroxyl function.

8. The product of claim 1, wherein the vitamin is selected from the group consisting of retinol, ascorbic acid and tocopherol.

9. The product of claim 1, wherein the ester is selected from the group consisting of dihydroxyacetone mono- and dipalmitate, ascorbyl palmitate, ascorbyl laurate, ascorbyl myristate, ascorbyl stearate, ascorbyl nicotinate, tocopheryl acetate, tocopheryl linoleate, retinyl palmitate, retinyl propionate, retinyl acetate, retinyl butyrate, retinyl octanoate, retinyl laurate, retinyl oleate and retinyl linoleate.

10. The product of claim 1, wherein the ester is selected from the group consisting of ascorbyl palmitate, ascorbyl laurate, ascorbyl myristate, ascorbyl stearate, ascorbyl nicotinate, tocopheryl acetate, tocopheryl linoleate, retinyl palmitate, retinyl propionate, retinyl acetate, retinyl butyrate, retinyl octanoate, retinyl laurate, retinyl oleate and retinyl linoleate.

11. The product of claim 1, which is packaged such that the lipase and the precursor are not in contact with each other.

12. The product of claim 11, wherein the lipase and the precursor are packaged in separate compartments.

13. The product of claim 1, wherein the lipase and/or the precursor and/or the $C_6$ to $C_{22}$ alcohols are in an encapsulated form.

14. The product of claim 1, wherein the lipase and/or the precursor and/or the $C_6$ to $C_{22}$ alcohols are in the form of microcapsules or microgranules.

15. The product of claim 1, wherein the lipase is selected from the group consisting of enzymes of classification EC 3.1.1.3.

16. The product of claim 1, comprising 0.05 to 30% by weight of the lipase.

17. The product of claim 1, comprising 0.1 to 10% by weight of the lipase.

18. The product of claim 1, comprising 0.1 to 50% by weight of the precursor.

19. The product of claim 1, wherein, when the precursor is a vitamin ester, the product comprises 0.5 to 10% by weight of the precursor.

20. The product of claim 1, wherein the $C_6$ to $C_{22}$ alcohol has a carbon chain is which is saturated or unsaturated, and linear, branched or cyclic.

21. The product of claim 1, wherein the $C_6$ to $C_{22}$ alcohols are selected from the group consisting of cetyl alcohol, stearyl alcohol, isostearyl alcohol, cetylstearyl alcohol, and behenylstearyloctyldodecanol.

22. The product of claim 1, wherein products comprising cetyl alcohol and ascorbyl palmitate or stearyl alcohol and retinyl palmitate are excluded.

23. The product of claim 1, wherein products comprising at least one member selected from the group consisting of cetyl alcohol, ascorbyl palmitate, stearyl alcohol and retinyl palmitate, are excluded.

24. The product of claim 1, which is in the form of a salve or ointment that is suitable for topical application to skin.

25. A method of preparing the product of claim 1, comprising combining the lipase, the precursor, and the alcohol.

26. A method of treating skin, comprising applying the product of claim 1 to the skin.

27. A method of treating skin, comprising applying to the skin a lipase, at least one precursor of a vitamin, wherein the precursor is an ester containing at least one ester functional group having a linear or branched, saturated or unsaturated chain containing from 2 to 25 carbon atoms; and at least one $C_6$ to $C_{22}$ alcohol, wherein the weight ratio of the alcohol to the precursor is 0.25 to 30/1, with the proviso applying (1) cetyl alcohol/ascorbyl palmitate at a weight ratio of 4/1, or (2) stearyl alcohol/retinyl palmitate at a weight ratio of 1/0.6 is excluded.

* * * * *